United States Patent
Sakaki et al.

(10) Patent No.: US 8,252,531 B2
(45) Date of Patent: Aug. 28, 2012

(54) NONSPECIFIC HYBRIDIZATION INHIBITORS, CLINICAL EXAMINATION REAGENTS AND CLINICAL EXAMINATION METHOD

(75) Inventors: Shujiro Sakaki, Tsukuba (JP); Kenshiro Shuto, Tsukuba (JP); Mamoru Tsuchida, Noda (JP); Yoshihiro Ashihara, Hannou (JP); Mitsuo Isomura, Kawagoe (JP)

(73) Assignee: NOF Corporation, Tokyo (JP)

( * ) Notice: Subject to any disclaimer, the term of this patent is extended or adjusted under 35 U.S.C. 154(b) by 2080 days.

(21) Appl. No.: 10/476,069

(22) PCT Filed: Apr. 25, 2002

(86) PCT No.: PCT/JP02/04128
§ 371 (c)(1),
(2), (4) Date: Feb. 11, 2004

(87) PCT Pub. No.: WO02/088389
PCT Pub. Date: Nov. 7, 2002

(65) Prior Publication Data
US 2004/0219546 A1    Nov. 4, 2004

(30) Foreign Application Priority Data
Apr. 26, 2001 (JP) ................................. 2001-128699

(51) Int. Cl.
*C12Q 1/68* (2006.01)
(52) U.S. Cl. .................. 435/6.1; 435/6.15; 526/277
(58) Field of Classification Search .............. None
See application file for complete search history.

(56) References Cited

U.S. PATENT DOCUMENTS

| 7,166,476 B2 * | 1/2007 | Shigenobu et al. | 436/536 |
| 2004/0219546 A1 * | 11/2004 | Sakaki et al. | 435/6 |
| 2010/0222226 A1 * | 9/2010 | Ishihara et al. | 506/9 |

FOREIGN PATENT DOCUMENTS

| EP | 0 580 435 A1 | 1/1994 |
| EP | 580435 A1 * | 1/1994 |
| EP | 1 095 665 A1 | 5/2001 |
| EP | 1 206 946 A1 | 5/2002 |
| EP | 1 245 636 A1 | 10/2002 |
| JP | 04-346920 * | 7/1994 |
| JP | 6-189794 A1 | 7/1994 |
| JP | 2002-22740 A1 | 1/2002 |
| WO | WO98/22162 * | 5/1998 |
| WO | WO-98/22162 A1 | 5/1998 |
| WO | WO 2007/043498 A1 * | 4/2007 |
| WO | WO 2012/012694 A2 * | 1/2012 |

OTHER PUBLICATIONS

Bowie et al (Science, 1990, 257:1306-1310).*
Kazuhiko Ishihara et al., "Preparation of Phospholipid Polymers and Their properties as Polymer Hydrogel Membranes", Polymer Journal, vol. 22, No. 5, (1990), pp. 355-360.
Shujiro Sakaki et al., "Stabilization of an antibody conjugated with enzyme by 2-methacryloyloxyethyl phosphorylcholine copolymer in enzyme-linked immunosorbent assay", Journal of Biomedical Materials Research, Wiley, New York, vol. 47, No. 4, 1999, pp. 523-528.
S. Patterson et al., "DNA probes bind non-specifically to eosinphils during in situ hybridization: carbol chromotrope blocks binding to eosinphils but does not inhibit hybridization to specific nucleotide sequences", Journal of Virological Methods, 23 (1989), pp. 105-109.
Shujiro Sakaki et al., "MPC polymer ni yoru 1 Enki Tagata (SNPs) no Kokateki na Ninshiki", The Society of Polymer Science, Japan, Yokoshu, May 2001, vol. 50, No. 5, p. 992.
Shujiro Sakaki et al., "DNA/MPC Polymer Fukugotai no Tokusei", The Society of Polymer Science, Japan, Sep. 2000, vol. 49, No. 13, pp. 3872-3873.

* cited by examiner

*Primary Examiner* — Nita M Minnifield
(74) *Attorney, Agent, or Firm* — Fish & Richardson P.C.

(57) ABSTRACT

The present invention relates to an inhibitor capable of increasing accuracy of the reaction in hybridization, and inhibiting nonspecific hybridization, a clinical diagnostic reagent, and a method of clinical analysis whereby nonspecific hybridization in clinical analysis is inhibited, and a target nucleic substance is detected easily with high accuracy. The inhibitor and the clinical diagnostic reagent contains polymer (H) having a nonspecific hybridization inhibitory action. The polymer has in its molecule at least one of carboxyl and sulfone groups, and phosphorylcholine-like groups, and has a weight average molecular weight of 1000 to 5000000. The method of clinical analysis includes contacting a sample with a test agent capable of hybridizing with a specific nucleic substance in the presence of the inhibitor.

3 Claims, No Drawings

NONSPECIFIC HYBRIDIZATION INHIBITORS, CLINICAL EXAMINATION REAGENTS AND CLINICAL EXAMINATION METHOD

FIELD OF ART

The present invention relates to inhibitors for inhibiting nonspecific hybridization in detecting a target nucleic substance in a sample in the field of clinical analysis and the like, clinical diagnostic reagents containing the inhibitor, and a method of clinical analysis using the inhibitor.

BACKGROUND ART

In the art of clinical analysis, detection of nucleic substances such as DNAs and RNAs is made through hybridization. This method involves bringing a labeled sample into contact with a solid phase on which a DNA or the like of a sequence complementary to the target nucleic substance is fixed, washing away other materials than the target nucleic substance, and measuring the activity of the labeled material bound to the solid phase.

In the field of clinical analysis, by detecting a target nucleic substance through hybridization, the sequence of the nucleic substance is required to be recognized precisely.

In evaluating a sample by hybridization, it is conventionally and widely known to add surface active agents such as sodium dodecyl sulfate (abbreviated as SDS) or N-lauroyl sarcocine (abbreviated as N-LS); or proteins such as bovine serum albumin (abbreviated as BSA) or casein, for inhibiting nonspecific hybridization. However, such surface active agents and proteins have little nonspecific hybridization inhibitory action, so that the sequence of the nucleic substance cannot be recognized precisely.

Patrick et al. (Nature Biotechnology, 17, 365-370 (1999)) propose to inhibit binding of SNPs of a DNA by applying electrical current on the surface of a DNA chip. This method, however, requires dedicated DNA chips, and cannot be applied to every existing DNA chip.

On the other hand, polymers having a phosphorylcholine-like group are under examination for their possible use in the field of clinical analysis. Polymers having a phosphorylcholine-like group are known to have excellent biocompatibilities such as blood compatibility, ability to inactivate complements, and nonadsorbability of biomaterials, as well as excellent antifouling property and moisture holding property, due to their structures similar to phosphlipids originated from biomembrane. Researches and developments in synthesis and use of the polymers have been actively made for developing bio-related materials that make the most of these properties. JP-7-5177-A, JP-7-83923-A, and JP-10-114800-A disclose highly accurate clinical analysis techniques in which polymers having a phosphorylcholine group inhibit adsorption of proteins by a vessel.

However, it is not known that the sequence of a nucleic substance may be recognized precisely, i.e., nonspecific hybridization may be inhibited, by using particular polymers having phosphorylcholine groups.

DISCLOSURE OF THE INVENTION

It is an object of the present invention to provide a nonspecific hybridization inhibitor that increases accuracy of the reaction in hybridization, and inhibits nonspecific hybridization.

It is another object of the present invention to provide a clinical diagnostic reagent that inhibits nonspecific hybridization during hybridization for clinical analysis, and enables detection of a target nucleic substance with high efficiency and accuracy.

It is yet another object of the present invention to provide a method of clinical analysis whereby nonspecific hybridization in clinical analysis is inhibited, and a target nucleic substance is detected easily with high accuracy.

According to the present invention, there is provided a nonspecific hybridization inhibitor comprising a polymer (H) having a nonspecific hybridization inhibitory action, said polymer having in its molecule at least one of carboxyl and sulfone groups, and phosphorylcholine-like groups, and having a weight average molecular weight of 1000 to 5000000.

According to the present invention, there is also provided a clinical diagnostic reagent comprising the above inhibitor and a test agent.

According to the present invention, there is further provided a method of clinical analysis comprising the steps of:
(1) contacting a sample with a test agent capable of hybridizing with a specific nucleic substance in the presence of the above inhibitor under particular conditions for hybridizing said specific nucleic substance with said test agent, and
(2) detecting a reactant generated by hybridization with said test agent in step (1).

PREFERRED EMBODIMENT OF THE INVENTION

The inhibitor according to the present invention contains a polymer (H) having a nonspecific hybridization inhibitory action, which polymer has in its molecule at least one of carboxyl and sulfone groups, and phosphorylcholine-like groups (abbreviated as PC group), and has a particular weight average molecular weight.

In the polymer (H), the ratio of the at least one of carboxyl and sulfone groups to the PC groups is not particularly limited as long as the polymer (H) has the nonspecific hybridization inhibitory action, and may suitably be decided depending on the kinds and ratio of the monomers used in preparing the polymer (H) to be discussed later, or the molecular weight of the polymer (H).

The polymer (H) may optionally have other groups as long as the polymer (H) has the essential groups as mentioned above, has the particular molecular weight, and has the nonspecific hybridization inhibitory action. Examples of such other groups may include various groups such as phosphoric acid, betaine, primary amino, secondary amino, tertiary amino, quaternary ammonium, acrylamide, methacrylamide, 4-butane lactam(2-pyrrolidone), 4-butane lactim(2-hydroxy-1-pyrroline), 6-hexane lactam($\epsilon$-caprolactam), polyethylene oxide, polypropylene oxide, and block or random polymers of polyethylene oxide and polypropylene oxide. The examples of the other groups may also include groups derived from various hydrophobic monomers to be discussed later.

The content of such other groups in the polymer (H) may suitably be selected from the range of content that will not disturb or will enhance the objects of the present invention.

The molecular weight of the polymer (H) is usually 1000 to 5000000, preferably 10000 to 2000000, by weight average molecular weight. It is not preferred that the molecular weight is less than 1000 since sufficient inhibition of the nonspecific hybridization is hard to be achieved, and that the molecular weight is over 5000000 since the viscosity of the polymer (H) is too high, which may inhibit hybridization.

The polymer (H) may be prepared, for example, by polymerizing a monomer having a PC group (referred to as PC monomer) and a monomer having a sulfone group (referred to as SA monomer) and/or a monomer having a carboxyl group (referred to as CA monomer), and optionally other monomers such as a hydrophobic monomer as needed, by conventional radical polymerization. Each monomer used in the polymerization does not have to be of a single kind, but may be of two or more kinds.

Examples of the PC monomer may include monomers represented by the formula (1):

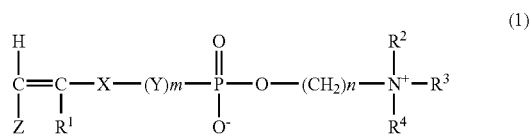

In the formula (1), X stands for a divalent organic residue, Y stands for an alkyleneoxy group having 1 to 6 carbon atoms, and Z stands for a hydrogen atom or $R^5O(C=O)-$, wherein $R^5$ stands for an alkyl or hydroxyalkyl group having 1 to 10 carbon atoms. $R^1$ in the formula (1) stands for a hydrogen atom or a methyl group, and $R^2$, $R^3$, and $R^4$ are the same or different groups, and each stands for a hydrogen atom, or an alkyl or hydroxyalkyl group having 1 to 6 carbon atoms. m is 0 or 1, and n denotes an integer of 1 to 4.

X in the formula (1) may be, for example, $-C_6H_4-$, $-C_6H_{10}-$, $-(C=O)O-$, $-O-$, $-CH_2O-$, $-(C=O)NH-$, $-O(C=O)-$, $-O(C=O)O-$, $-C_6H_4O-$, $-C_6H_4CH_2O-$, or $-C_6H_4(C=O)O-$. Y in the formula (1) may be, for example, a methyloxy, ethyloxy, propyloxy, butyloxy, pentyloxy, or hexyloxy group. $R^5$ in the formula for Z may be, for example, an alkyl group having 1 to 10 carbon atoms, such as a methyl, ethyl, propyl, butyl, pentyl, hexyl, heptyl, octyl, nonyl, or decyl group; or a hydroxyalkyl group having 1 to 10 carbon atoms, such as a hydroxymethyl, 2-hydroxyethyl, 3-hydroxypropyl, 2-hydroxypropyl, 4-hydroxybutyl, 2-hydroxybutyl, 5-hydroxypentyl, 2-hydroxypentyl, 6-hydroxyhexyl, 2-hydroxyhexyl, 7-hydroxyheptyl, 2-hydroxyheptyl, 8-hydroxyoctyl, 2-hydroxyoctyl, 9-hydroxynonyl, 2-hydroxynonyl, 10-hydroxydecyl, or 2-hydroxydecyl group.

Examples of the PC monomer may include 2-((meth)acryloyloxy)ethyl-2'-(trimethylammonio)ethyl phosphate, 3-((meth)acryloyloxy)propyl-2'-(trimethylammonio)ethyl phosphate, 4-((meth)acryloyloxy)butyl-2'-(trimethylammonio)ethyl phosphate, 5-((meth)acryloyloxy)pentyl-2'-(trimethylammonio)ethyl phosphate, 6-((meth)acryloyloxy)hexyl-2'-(trimethylammonio)ethyl phosphate, 2-((meth)acryloyloxy)ethyl-2'-(triethylammonio)ethyl phosphate, 2-((meth)acryloyloxy)ethyl-2'-(tripropylammonio)ethyl phosphate, 2-((meth)acryloyloxy)ethyl-2'-(tributylammonio)ethyl phosphate, 2-((meth)acryloyloxy)ethyl-2'-(tricyclohexylammonio)ethyl phosphate, 2-((meth)acryloyloxy)ethyl-2'-(triphenylammonio)ethyl phosphate, 2-((meth)acryloyloxy)ethyl-2'-(trimethanol ammonio)ethyl phosphate, 2-((meth)acryloyloxy)propyl-2'-(trimethylammonio)ethyl phosphate, 2-((meth)acryloyloxy)butyl-2'-(trimethylammonio)ethyl phosphate, 2-((meth)acryloyloxy)pentyl-2'-(trimethylammonio)ethyl phosphate, 2-((meth)acryloyloxy)hexyl-2'-(trimethylammonio)ethyl phosphate, 2-(vinyloxy)ethyl-2'-(trimethylammonio)ethyl phosphate, 2-(allyloxy)ethyl-2'-(trimethylammonio)ethyl phosphate, 2-(p-vinylbenzyloxy)ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio) ethyl phosphate, 2-(vinyloxycarbonyl)ethyl-2'-(trimethylanmmonio)ethyl phosphate, 2-(allyloxycarbonyl)ethyl-2'-(trimethylammonio)ethyl phosphate, 2-(acryloylamino)ethyl-2'-(trimethylammonio)ethyl phosphate, 2-(vinylcarbonylamino)ethyl-2'-(trimethylammonio) ethyl phosphate, ethyl-(2'-trimethylammonioethylphosphorylethyl) fumarate, butyl-(2'-trimethylammonioethylphophorylethyl) fumarate, hydroxyethyl-(2'-trimethylammonioethylphosphorylethyl) fumarate, ethyl-(2'-trimethylammonioethylphosphorylethyl) maleate, butyl-(2'-trimethylammonioethylphosphorylethyl) maleate, and hydroxyethyl-(2'-trimethylammonioethylphosphorylethyl) maleate.

Among these examples, 2-((meth)acryloyloxy)ethyl-2'-(trimethylammonio) ethyl phosphate is preferred, and in particular 2-(methacryloyloxy)ethyl-2'-(trimethylammonio) ethyl phosphate (i.e., 2-(methacryloyloxy) ethylphosphorylcholine) (abbreviated as MPC) is preferred for its availability. As used herein, (meth)acryloyl means methacryloyl and/or acryloyl.

The PC monomer may be prepared by a conventional method, for example, by reacting 2-hydroxyethyl methacrylate and 2-bromoethylphosphoryl dichloride in the presence of a tertiary base, of which reaction product is further reacted with a tertiary amine, as disclosed in JP-54-63025-A, or by reacting a polymerizable monomer having a hydroxyl group and a cyclic phosphorus compound, followed by ring-opening with a tertiary amine, as disclosed in JP-58-154591-A.

Examples of the SA monomer may include 2-methylpropane sulfonate, 2-dimethylpropane sulfonate, styrene sulfonate, and 2-sulfoethyl methacrylate. Among these examples, 2-methylpropane sulfonate, 2-dimethylpropane sulfonate, and styrene sulfonate are preferred.

Examples of the CA monomer may include (meth) acrylic acid, 3-pentenoic acid, 4-pentenoic acid, 3-acryloxypropionic acid, 2-(meth)acryloyloxyethylphthalic acid. Among these examples, methacrylic acid and acrylic acid are preferred.

The hydrophobic monomer may be a monomer represented by the formula (2):

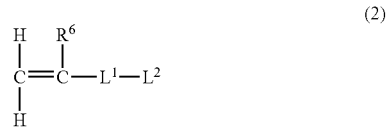

In the formula (2), $R^6$ stands for a hydrogen atom or a methyl group, $L^1$ stands for $-C_6H_4-$, $-C_6H_{10}-$, $-(C=O)O-$, $-O-$, $-(C=O)NH-$, $-O(C=O)-$, or $-O(C=O)O-$, and $L^2$ stands for a hydrogen atom, $-(CH_2)$g-$L^3$, or $((CH_2)_p-O)_h$-$L^3$, wherein g and h each denotes an integer of 1 to 24, p denotes an integer of 3 to 5, and $L^3$ stands for a hydrogen atom, a methyl group, $-C_6H_5$, or $-OC_6H_5$.

Examples of the hydrophobic monomer may include straight or branched alkyl (meth)acrylates, such as methyl (meth)acrylate, ethyl (meth)acrylate, butyl (meth)acrylate, 2-ethylhexyl (meth)acrylate, lauryl (meth)acrylate, or stearyl (meth)acrylate; cyclic alkyl (meth)acrylates such as cyclohexyl (meth)acrylate; aromatic ring (meth)acrylates such as benzyl (meth)acrylate or phenoxyethyl (meth)acrylate; polyalkylene glycol (meth) acrylates such as polypropylene glycol (meth)acrylate; styrene monomers such as styrene, methylstyrene, or chloromethylstyrene; vinyl ether monomers such as methylvinyl ether or butylvinyl ether; and vinyl ester monomers such as vinyl acetate or vinyl propionate. Among these examples, butyl methacrylate and lauryl methacrylate are preferred.

The polymer (H) may be a polymer having the particular molecular weight mentioned above and obtained by polymerizing a monomer composition containing 5 to 95 mol %, preferably 10 to 90 mol % of the PC monomer and 5 to 95 mol %, preferably 10 to 90 mol % of at least one of the SA and CA monomers, or a monomer composition containing 5 to 90 mol %, preferably 10 to 85 mol % of the PC monomer, 5 to 90 mol %, preferably 10 to 85 mol % of at least one of the SA and CA monomers, and 5 to 60 mol %, preferably 5 to 50 mol % of the hydrophobic monomer.

As used herein, the phrase "at least one of the SA and CA monomers" includes all the embodiments wherein either the SA or CA monomer is contained alone, and wherein both the SA and CA monomers are contained together. Further, each of the monomer compositions mentioned above may optionally contain other monomers, in addition to the PC monomer, the SA monomer, the CA monomer, and the hydrophobic monomer. In each of the monomer compositions, the content of such other monomers is usually not higher than 10 mol %, preferably 5 mol %. In some embodiments, it is rather preferred not to contain such other monomers.

If the contents of the PC monomer and at least one of the SA and CA monomers in each monomer composition are all less than 5 mol %, the nonspecific hybridization cannot be inhibited sufficiently, thus not being preferred. The polymer (H) may be prepared by conventional radical copolymerization.

There is no particular limitation imposed on the present inhibitor as long as the inhibitor contains the polymer (H). The present inhibitor may be used by adding the inhibitor to the hybridization system to mix so that the content of the polymer (H) in the hybridization system is usually 0.0001 to 20 wt %, preferably 0.001 to 10 wt %. If the content of the polymer (H) is less than 0.0001 wt %, the nonspecific hybridization inhibitory action may not be achieved sufficiently, whereas if over 20 wt %, the viscosity of the hybridization system is too high, which may inhibit the hybridization reaction, thus not being preferred.

The inhibitor of the present invention may optionally contain other components, such as surface active agents, solvents, and preservatives, as long as the effects of the present invention are not impaired. The inhibitor may be in the form of powders or a solution, but the solution form is preferred in use.

The clinical diagnostic reagent of the present invention is a test agent kit including the present inhibitor and a test agent. The test agent may be any nucleic substance as long as it hybridizes with the particular nucleic substance to be detected, and may be, for example, a test agent used in conventional clinical diagnostic reagents depending on the target.

As used herein, the nucleic substance means any one or more groups of compounds containing carbohydrate molecules, such as pentose or hexose, having one or more phosphorus molecules bound thereto, each of which carbohydrate molecules binds to a base such as adenine derived from purine or thymine derived from pyrimidine. Specifically, naturally occurring nucleic acid molecules include genomic DNAs, genomic RNAs, and various types of RNAs, such as mRNAs, tRNAs, and rRNAs, and also cDNAs. Further, the nucleic substance also includes synthesized DNAs or hybrids of naturally occurring DNAs and synthesized DNAs.

The nucleic substance may be either single or double stranded, linear or circular, or plasmids, or oligonucleotide or polynucleotide. The nucleic substance may include bases or base pairs having from about 10 to about 20000 bases (20 kb). In addition to such naturally occurring substances, for example, those obtained from such sources as ATCC or Gene Bank (GenBank) Libraries, and synthetic compositions, i.e., nucleic acid-like materials, may also be included. Synthetic nucleic acids may be prepared by a variety of solution or solid phase methods. Generally, solid phase synthesis is preferred. Synthesis of nucleic acids by phosphite-triester, phosphotriester, and H-phosphonate chemistries are widely available. (Itakura, U.S. Pat. No. 4,458,066 and U.S. Pat. No. 4,500,707; Garuthers et al., Genetic Engineering, 4:1-17 (1982); Jones, chapter 2, Atkinson, et al., chapter 3, and Sproat, et al., chapter 4, in Oligonucleotide Synthesis: A Practical Approach, Gait (ed.), IRL Press, Washington, D.C. (1984)).

In the clinical diagnostic reagent of the present invention, the content of the present inhibitor may suitably be selected depending on the method of clinical analysis and the target to be detected, and may be such that the content of the polymer (H) of the inhibitor in the hybridization system is usually 0.0001 to 20 wt %, preferably 0.001 to 10 wt %.

The clinical diagnostic reagent of the present invention may optionally contain other compounds required for the test agent, such as various additives and solvents usually contained in clinical diagnostic reagents. The usage of the clinical diagnostic reagent is not particularly limited, and the diagnostic reagent may be used, for example, with reference to the method of clinical analysis according to the present invention to be discussed later.

The method of clinical analysis according to the present invention includes step (1) of first contacting a sample with a test agent capable of hybridizing with a specific nucleic substance, in the presence of the inhibitor of the present invention under the particular conditions for hybridizing the specific nucleic substance with the test agent.

Step (1) may be performed using the inhibitor of the present invention or the clinical diagnostic reagent of the present invention. Step (1) may be performed, for example, by adding the present inhibitor to a system containing a sample and a test agent, and keeping the system under the particular conditions; by keeping a system containing a sample and a test agent under the particular conditions, and adding the present inhibitor to the system; or by adding the present inhibitor to a sample and/or a test agent in advance, and then contacting the sample and the test agent under the particular conditions.

Step (1) may be carried out, for example, by adding the present inhibitor upon or after fixing the test agent on a carrier, and hybridizing the test agent with a sample. In this case, the inhibitor of the present invention may be in the form of either a solution or powders, and may preferably be in a solution form for its readiness of homogenization with the reaction system.

The carrier may be, for example, a membrane such as a nitrocellulose, nylon, or PVDF membrane; or a plate or a flat plate such as those made of polystyrene, polypropylene, glass, or metal, but not limited to these examples. The test agent may be fixed to the carrier for example by electrostatic binding, by using ionicity, by covalent bonding by UV rays or the like, or by covalent bonding using a crosslinking reagent.

Alternatively, step (1) may also be performed in a solution without the carrier. Examples of such method may include polymerase chain reaction (PCR), sequence reaction, RNAdependent DNA synthesis using a reverse transcriptase, or various transcription reactions using a DNA polymerase employed in gene engineering.

In step (1), the particular conditions for hybridizing the specific nucleic substance with the test agent may suitably be selected, for example, from suitable conditions for Southern hybridization when the specific nucleic substance to be detected is a DNA, or from suitable conditions for Northern hybridization when the specific nucleic substance to be detected is an RNA.

The method of clinical analysis according to the present invention includes step (2) of detecting a reactant generated by hybridization with the test agent in step (1).

In step (2), the reactant may be detected, for example, by labeling in accordance with a conventional labeling technique for detecting a reactant, and measuring the activity or the like of the label. The labeling may be performed with radioisotopes such as $^{32}P$, $^{14}C$, or $^{3}H$, fluorescent dyes, enzyme proteins, or antibodies to various antigenic substances. The labeled compounds may be prepared by using a DNA polymerase with the labeling reagent as the substrate, or by chemical reactions. The method of detecting the reactant may suitably be selected depending on the labeling method. For example, when the labeling is performed with a radioisotope, the labeled reactant may be detected by means of a scintillation counter or auto radiography; when labeled with a fluorescent dye, by means of a detector utilizing lasers; and when labeled with an enzyme protein or various antigens, by means of detection of chemiluminescence, fluorescence, or coloring of the enzyme substrate.

The method of clinical analysis according to the present invention is not particularly limited as long as the method includes steps (1) and (2) discussed above, and may easily be practiced utilizing various conventional methods. An embodiment utilizing Southern blot hybridization is discussed below. The following discussion does not include the description of the inhibitor of the present invention, but the method of clinical analysis according to the present invention may be performed by suitably adding the present inhibitor at various time points and in the preferred amount mentioned above.

First, from biological tissues such as blood, genomic DNAs are prepared with ISOGEN® chemical isolation reagent registered trademark owned by MOLECULAR RESEARCH CENTER, INC., Cincinnati, Ohio). The resulting DNAs are separated by 0.7% agarose gel electrophoresis. After the completion of the electrophoresis, the gel is immersed in a 0.25 N hydrochloric acid solution at room temperature for 15 minutes, and then in a 0.4 N sodium hydroxide solution at room temperature for 30 minutes under gentle shaking. On a blot table previously prepared, the resulting gel, a GENE SCREEN PLUS® membrane (registered trademark owned by E.I. DU PONT DE NEMOURS AND COMPANY), 3MM filter papers (manufactured by WHATMAN plc), KIMTOWELS® paper wipers (registered trademark owned by KIMBERLY-CLARK CORPORATION), and a weight are placed on top of another in this order, and left overnight to transcript the DNAs in the gel to the Gene Screen Plus membrane. When the transcription is completed, the Gene Screen Plus membrane is immersed in a 0.5 M Tris buffer at room temperature for 15 minutes, dried at room temperature, and baked at 80° C. for 2 hours. The resulting membrane is shaken in 2×SSC (0.3 M sodium chloride, 0.03 M sodium citrate), and then immersed in a rapid hybridization buffer (manufactured by Amersham Pharmacia Biotech) at 65° C. for 15 minutes under shaking 10 for pre-hybridization. A solution of target DNA probes ($^{32}P$ labeled) previously labeled with [$\gamma^{32}$P]-dCTP by nick translation is added to the hybridization buffer, and the hybridization is effected at 65° C. for 2 hours. The membrane is shaken in 0.1×SSC (0.015 M sodium chloride, 0.0015 M sodium citrate) at 65° C. for 15 minutes. This operation is repeated twice to wash away excess probes. Excess moisture is removed on filter papers, and X-ray film is exposed to the radioactive rays from the probes at −70° C. for 24 hours, and developed. The objective bands are quantified by a densitometer. (Molecular Cloning: A LABORATORY MANUAL, 2nd edition, Cold Spring Harbor Laboratory Press (1989)).

EXAMPLES

The present invention will now be explained in more detail with reference to Examples and Comparative Examples, but the present invention is not limited thereto.

Synthesis Example 1

19.4 g of MPC and 0.6 g of methacrylic acid (abbreviated as MA) were dissolved in 40 g of water, and poured into a four neck flask. The solution was bubbled with nitrogen for 30 minutes, 1.6 g of succinic peroxide was added at 60° C., and the mixture was polymerized for 8 hours. The polymerization solution was added dropwise to 3 L of acetone under stirring. The resulting precipitate was taken out by filtration, and vacuum dried at room temperature for 48 hours, to obtain 14.6 g of polymer powders (abbreviated as Polymer (P1)). The molecular weight of Polymer (P1) was analyzed by gel permeation chromatography (GPC), wherein the elution solvent was a 20 mM phosphate buffer (pH 7.4), the reference material was polyethylene glycol, and the detection was made in accordance with the refractive index. Further, the compositional ratio of and the groups contained in Polymer (P1) were determined by $^{1}$H-NMR. The results are shown in Table 1.

Synthesis Examples 2 to 5

Polymer powders were prepared in the same way as in Synthesis Example 1, except that the kinds and the compositional ratio of the monomers used in Synthesis Example 1 were changed as shown in Table 1. The obtained polymer powders were referred to as Polymers (P2) to (P5). The same analyses as in Synthesis Example 1 were performed. The results are shown in Table 1.

Synthesis Examples 6 and 7

Polymer powders were prepared in the same way as in Synthesis Example 1, except that the kinds and the compositional ratio of the monomers used in Synthesis Example 1 were changed as shown in Table 1, 40 g of water was replaced with 120 g of isopropanol, and 1.6 g of succinic peroxide was replaced with 0.7 g of azobis isobutyronitrile (abbreviated as AIBN). The obtained polymer powders were referred to as Polymers (P6) and (P7). The same analyses as in Synthesis Example 1 were performed. The results are shown in Table 1, wherein BMA is an abbreviation for butyl methacrylate.

Synthesis Examples 8 to 10

Polymer powders were prepared in the same way as in Synthesis Example 1, except that the kinds and the compositional ratio of the monomers used in Synthesis Example 1 were changed as shown in Table 2, and the amount of succinic peroxide was 0.65 g. The obtained polymer powders were referred to as Polymers (P8) to (P10). The same analyses as in Syntheses Example 1 were performed. The results are shown in Table 2, wherein MPs is an abbreviation for 2-methylpropanesulfonic acid.

Synthesis Examples 11 to 12

Polymer powders were prepared in the same way as in Synthesis Example 1, except that the kinds and the compositional ratio of the monomers used in Synthesis Example 1 were changed as shown in Table 2, the amount of water was 120 g, and the amount of succinic peroxide was 0.23 g. The obtained polymer powders were referred to as Polymers (P11) to (P12). The same analyses as in Synthesis Example 1 were performed. The results are shown in Table 2, wherein Am is an abbreviation for acrylamide, Vp for N-vinyl-2-pyrrolidone, and MANa for sodium methacrylate.

PUC"-5': CCCAGTCACGTCGTTGTAAA-3' (SEQ ID NO: 4)

100 μl/well of a 25 pmol/ml PUC-NH$_2$ solution in a 50 mM phosphate buffer (pH 8.5) mixed with 1 mM EDTA (abbreviated as E-NaPB) was dispensed into a DNA-BIND 96-well plate (manufactured by Corning Incorporated), and incubated overnight at 4° C. (immobilization of PUC-NH$_2$) Then each well was cleared of the PUC-NH$_2$ solution, and washed three times with Dulceco's PBS (abbreviated as D-PBS). 200 μl/well of the E-NaPB solution mixed with 3% BSA (abbreviated as B-E-NaPB) was added, and incubated at 37° C. for 1 hour (blocking operation-1). Then each well was cleared of the B-E-NaPB to prepare a PUC-NH$_2$-immobilized plate.

In the PUC-NH$_2$-immobilized plate, 3.2 wt % of Polymer (P1), 0.2 μmol/ml each of PUC, PUC', and PUC", and a 75 mM sodium citrate solution containing 750 mM NaCl (abbreviated as 5×SSC) were added in an amount of 100 μl/well, and

TABLE 1

|  |  | Synthesis Example 1 | Synthesis Example 2 | Synthesis Example 3 | Synthesis Example 4 | Synthesis Example 5 | Synthesis Example 6 | Synthesis Example 7 |
|---|---|---|---|---|---|---|---|---|
| Kind of Polymer |  | (P1) | (P2) | (P3) | (P4) | (P5) | (P6) | (P7) |
| Monomer (A) | MPC | 19.4 g | 17.1 g | 15.5 g | 12.0 g | 20.0 g | 9.79 g | 12.3 g |
| Composition (B) | MA | 0.6 g | 2.2 g | 4.5 g | 8.0 g | — | 2.85 g | 1.79 g |
| (C) | BMA | — | — | — | — | — | 2.35 g | 5.92 g |
| Molar Ratio of Monomers |  | A/B = 90/10 | A/B = 70/30 | A/B = 50/50 | A/B = 30/70 | A/B = 100/0 | A/B/C = 40/40/20 | A/B/C = 40/20/40 |
| Polymer Compositional Ratio |  | A/B = 89/11 | A/B = 68/32 | A/B = 49/51 | A/B = 29/71 | A/B = 100/0 | A/B/C = 41/40/19 | A/B/C = 40/22/38 |
| Kinds of Groups Contained |  | —PC—COOH | —PC—COOH | —PC—COOH | —PC—COOH | —PC | —PC—COOH | —PC—COOH |
| Weight Average Molecular Weight |  | 153000 | 550000 | 1104000 | 653000 | 1030000 | 363000 | 56000 |

TABLE 2

|  |  | Synthesis Example 8 | Synthesis Example 9 | Synthesis Example 10 | Synthesis Example 11 | Synthesis Example 12 |
|---|---|---|---|---|---|---|
| Kind of Polymer |  | (P8) | (P9) | (P10) | (P11) | (P12) |
| Monomer (A) | MPC | 23.06 g | 17.62 g | 11.37 g | — | — |
| Composition | Am | — | — | — | 19.75 g | — |
|  | Vp | — | — | — | — | 22.52 g |
|  | E4 | — | — | — | — | — |
| (B) | MPs | 6.94 g | 12.38 g | 18.63 g | — | — |
|  | MANa | — | — | — | 10.25 g | 7.48 g |
| Molar Ratio of Monomers |  | A/B = 70/30 | A/B = 50/50 | A/B = 30/70 | A/B = 70/30 | A/B = 70/30 |
| Polymer Compositional Ratio |  | A/B = 70/30 | A/B = 48/52 | A/B = 33/67 | A/B = 66/34 | A/B = 71/29 |
| Kinds of Groups Contained |  | —PC—SO$_3$H | —PC—SO$_3$H | —PC—SO$_3$H | —COONa-amide | —COONa-pyrrolidone |
| Weight Average Molecular Weight |  | 622000 | 1070000 | 1016000 | 1197000 | 800000 |

Example 1-1

An oligo DNA having the 5'-terminal modified with an amino group (abbreviated as PUC-NH$_2$) for immobilization, a full match oligo DNA having the 5'-terminal modified with biotin and having a sequence complementary to PUC-NH$_2$ (abbreviated as PUC), and mismatch oligo DNAs having the 5'-terminal modified with biotin, which are SNPs of PUC, (abbreviated as PUC' and PUC"), each having the DNA sequence shown below, were used. PUC-NH$_2$, PUC, PUC', and PUC" are manufactured by ESPEC OLIGO SERVICE CORP.
PUC-NH$_2$: 5'-ACTGGCCGTCGTTTTACAACGTCGTGACTGGG-3' (SEQ ID NO: 1)
PUC-5': CCCAGTCACGACGTTGTAAA-3' (SEQ ID NO: 2)
PUC'-5': CCCAGTCACCACGTTGTAAA-3' (SEQ ID NO: 3)

incubated at 55° C. for 1 hour for hybridization. Each well was cleared of the solution, and washed twice with a 30 mM sodium citrate solution containing 300 mM NaCl (abbreviated as 2×SSC) at 55° C. 200 μl/well of the B-E-NaPB was added, and incubated at 37° C. for 30 minutes (blocking operation-2), and then each well was cleared of 10 the B-E-NaPB. 100 μl/well of an avidin-horseradish peroxidase (manufactured by SIGMA-ALDRICH CO.) solution diluted 10000 times with the B-E-NaPB (abbreviated as Avdin-HRP) was added, and incubated at 37° C. for 30 minutes (avidin-biotin reaction). Each well was then washed 15 three times with D-PBS, 100 μl/well of the substrate solution included in the HRP kit was added, and the mixture was incubated at 25° C. for 10 minutes (POD-substrate reaction). Subsequently, 100 μl/well of the reaction terminator included in the HRP kit was added, and the absorbance at 450 nm was measured by means of SPECTRA MAX250® (microplate reader, registered trademark owned by MOLECULAR DEVICES COR- PORATION). Incidentally, the HRP kit used herein was Coloring Kit T for Peroxidase (manufactured by SUMITOMO BAKELITE CO., LTD.).

From the results of the measurements, the ratios of (absorbance of PUC)/(absorbance of PUC') and (absorbance of PUC)/(absorbance of PUC") were determined. The results are shown in Table 3.

Examples 1-2 to 1-9 and Comparative Examples 1-1 to 1-2

Measurements were made in the same way as in Example 1-1, except that Polymer (P1) was replaced with each polymer shown in Table 3. The results are shown in Table 3.

Comparative Example 1-3

Measurements were made in the same way as in Example 1-1, except that the 5×SSC solution containing 3.2 wt % of Polymer (P1) and 0.2 pmol/ml each of PUC, PUC', and PUC" was replaced with a 5×SSC solution containing 0.2 pmol/ml each of PUC, PUC', and PUC". The results are shown in Table 3.

Comparative Example 1-4

Measurements were made in the same way as in Example 1-1, except that the 5×SSC solution containing 3.2 wt % of Polymer (P1) and 0.2 pmol/ml each of PUC, PUC', and PUC" was replaced with a 5×SSC solution containing 1.0% casein (manufactured by SIGMA-ALDRICH CO.) and 0.1% N-LS (manufactured by WAKO PURE CHEMICALS INDUSTRIES, LTD.). The results are shown in Table 3.

Comparative Example 1-5

Measurements were made in the same way as in Example 1-1, except that the 5×SSC solution containing 3.2 wt % of polymer (P1) and 0.2 µmol/ml each of PUC, PUC', and PUC" was replaced with 0.2 µmol/ml each of PUC, PUC', and PUC", and a 6×SSC solution containing 10 mg/ml FICOLL® 400 copolymer of epichlorohydrin and sucrose (registered trademark owned by AMERSHAM PHARMACIA BIOTECH, now PHARMACIA FINE CHEMICALS, INC.), 10 mg/ml polyvinylpyrrolidone, 10 mg/ml bovine serum albumin, and 0.5% SDS (Denhard's solution). The results are shown in Table 3.

TABLE 3

| Kind of Polymer (Abbreviation) | | (Absorbance of PUC)/(Absorbance of PUC') | (Absorbance of PUC)/(Absorbance of PUC") |
| --- | --- | --- | --- |
| Example 1-1 | (P1) | 4.5 | 2.0 |
| Example 1-2 | (P2) | 4.0 | 2.6 |
| Example 1-3 | (P3) | 2.7 | 2.4 |
| Example 1-4 | (P4) | 2.6 | 2.3 |
| Example 1-5 | (P6) | 4.0 | 2.7 |
| Example 1-6 | (P7) | 3.8 | 2.2 |
| Example 1-7 | (P8) | 3.1 | 2.1 |
| Example 1-8 | (P9) | 3.1 | 2.5 |
| Example 1-9 | (P10) | 3.2 | 2.4 |
| Comp. Ex. 1-1 | (P11) | 2.4 | 1.6 |
| Comp. Ex. 1-2 | (P12) | 2.5 | 1.8 |
| Comp. Ex. 1-3 | — | 2.0 | 1.0 |

TABLE 3-continued

| Kind of Polymer (Abbreviation) | | (Absorbance of PUC)/(Absorbance of PUC') | (Absorbance of PUC)/(Absorbance of PUC") |
| --- | --- | --- | --- |
| Comp. Ex. 1-4 | Other Inhibitor | 1.8 | 1.0 |
| Comp. Ex. 1-5 | Other Inhibitor | 1.7 | 1.0 |

From Table 3, it is understood that the ratios of the absorbance in full match (absorbance of PUC) to the absorbance in mismatch (absorbance of PUC' or PUC") are higher in Examples than in Comparative Examples. This means that the inhibitors used in Examples do not inhibit specific hybridization but inhibit nonspecific hybridization, to realize more accurate hybridization.

Production Example 1-1

Into a 96-well multiplate (manufactured by Nalge Nunc International, white), 150 µl/well of 0.2 mg/ml poly(lysine-phenylalanine) dissolved in 5×SSC was dispensed and left to stand still at room temperature for 20 hours. The plate was washed with a 50 mM phosphate buffer (pH 8.3). 200 µl/well of 650 µM 2-iminothiolane hydrochloride dissolved in a 200 mM phosphate buffer (pH 8.0) was added, and left to stand still at room temperature for 2 hours. The plate was washed with a 10 mM phosphate buffer (pH 7.0).

An oligonucleotide having the 5'-terminal modified with an amino linker (manufactured by Amersham Pharmacia Biotech) (sequence: 5'-CATTAGGGATCCAGCCGTGAAT-TCGTCACT-3') (SEQ ID NO: 5) for immobilization was dissolved in a 50 mM phosphate buffer (pH 7.0), and N-succinimidyl 4-maleimidobutyrate (abbreviated as GMBS) dissolved in dimethylformamide (abbreviated as DMF) was added in an amount five times the molar amount of the oligonucleotide. The reaction was effected at 37° C. for 90 minutes, and the unreacted GMBS was removed to obtain a maleimide-attached oligonucleotide. 25 pmol/well of this maleimide-attached oligonucleotide was dispensed into a 96-well multiplate previously treated with 2-iminothiolane hydrochloride, and reacted at room temperature for 90 minutes. After the reaction was completed, the supernatant was discarded, 250 µl/well of a 0.8 mM iodoacetamide solution was added, and the plate was left to stand at room temperature for 20 hours. Subsequently, the plate was washed with a 10 mM phosphate buffer (pH 7.0), and 250 µl/well of a 50 mM Tris-50 mM sodium chloride-1% BSA buffer was added, and the plate was left to stand at room temperature for 20 hours to thereby prepare an oligonucleotide-immobilized plate.

Production Example 1-2

4.8 mg of anti-AFP antibody clone No. 9, which reacts with AFP, was reacted with 39 µg of pepsin at 37° C. for 30 minutes, and purified through gel filtration column chromatography to obtain 2.4 mg of an F(ab')2 fraction. To the obtained fraction, 0.2 M 2-mercaptoethanolamine was added in an amount 1/20 times the volume of the F(ab')2 fraction, to thereby prepare the Fab' fraction by reduction.

A full match oligonucleotide having the 5'-terminal modified with an amino linker (manufactured by Amersham Pharmacia Biotech; sequence: 5'-AGTGACGAATTCACGGCTGGATCCCTAATG-3') (SEQ ID NO: 6) and a mismatch oligonucleotide having the 5'-terminal modified with an amino linker (manufactured by Amersham Pharmacia Biotech; sequence: 5'-GATTT-TAGCTCTTCTTTGGAGAAAGTGGTG-3') (SEQ ID NO: 7) were respectively dissolved in a 50 mM phosphate buffer (pH 7.0), and GMBS dissolved in DMF was added in an amount five times the molar amount of the oligonucleotide. The reaction was effected at 37° C. for 90 minutes, and the unreacted GMBS was removed to obtain maleimide-attached oligonucleotides. To each of the obtained maleimide-attached oligonucleotide, the Fab' fraction of the anti-AFP antibody was added in an amount 0.2 times the molar amount of the oligonucleotide, reacted, and desalted, to thereby prepare a full match anti-Fab' oligonucleotide complex (abbreviated as FM complex) and a mismatch anti-Fab' oligonucleotide complex (abbreviated as MM complex).

Example 2-1

An FM complex solution containing 0.2 wt % Polymer (P1) and an MM complex solution containing 0.2 wt % Polymer (P1) were dispensed into the oligonucleotide-immobilized plate prepared in Production Example 1-1 in an amount of 100 μl/well, and incubated at 37° C. for 30 minutes. The plate was washed with Tris-TritonX (referred to as washing solution (X) hereinbelow), and 100 μl of a 100 ng/ml diluted solution of AFP antigen was added and incubated at 37° C. for 1 hour. After the plate was washed with the washing solution (X), 200 μl of an AMPPD solution, a chemiluminescent substrate, was added, and incubated at 37° C. for 5 minutes. The plate was then read on a fluorescent plate reader ARVOsx (Wallac Beltold), and the ratio of (luminescence of FM complex)/(luminescence of MM complex) was determined from the measurement results. The results are shown in Table 4.

Examples 2-2 to 2-9 and Comparative Examples 2-1 to 2-3

Measurements were made following the same procedures as in Example 2-1, except that Polymer (P1) was replaced with each polymer shown in Table 4. The results are shown in Table 4.

Comparative Example 2-4

Measurements were made following the same procedures as in Example 2-1, except that the FM complex solution containing 0.2 wt % Polymer (P1) and the MM complex solution containing 0.2 wt % Polymer (P1) were replaced with the FM and MM complex solutions free of Polymer (P1), respectively. The results are shown in Table 4.

TABLE 4

|  | Kind of Polymer (Abbreviation) | (FM Luminescence)/ (MF Luminescence) |
| --- | --- | --- |
| Example 2-1 | (P1) | 3.2 |
| Example 2-2 | (P2) | 2.9 |
| Example 2-3 | (P3) | 12.8 |
| Example 2-4 | (P4) | 44.5 |
| Example 2-5 | (P6) | 8.4 |
| Example 2-6 | (P7) | 4.3 |
| Example 2-7 | (P8) | 3.4 |
| Example 2-8 | (P9) | 6.8 |
| Example 2-9 | (P10) | 39.1 |
| Comp. Ex. 2-1 | (P5) | 1.5 |
| Comp. Ex. 2-2 | (P11) | 1.9 |
| Comp. Ex. 2-3 | (P12) | 1.4 |
| Comp. Ex. 2-4 | — | 1.1 |

From Table 4, it is understood that the ratios of the luminescence of the FM complex to the luminescence of the MM complex are higher in Examples than in Comparative Examples. This means that the specific hybridization was not inhibited but the nonspecific hybridization was inhibited even at 37° C., thereby realizing more accurate hybridization.

Example 3-1

An oligo DNA having the 5'-terminal modified with an amino group (abbreviated as PUC2-$NH_2$) having the DNA sequence shown below for immobilization, the PUC having a sequence complementary to PUC2-$NH_2$, and the mismatch PUC' or PUC" having the 5'-terminal modified with biotin, which are SNPs of PUC, were used. PUC2-$NH_2$ is manufactured by ESPEC OLIGO SERVICE CORP.
PUC2-$NH_2$: 5'-($CH_2$)$_{12}$TTTACAACGTCGTGACTGGG-3' (SEQ ID NO: 8)
100 μl/well of a 25 pmol/ml PUC2-$NH_2$ solution in E-NaPB was dispensed into a DNA-BIND 96-well plate (manufactured by Corning Incorporated), and incubated overnight at 4° C. (immobilization of PUC2-$NH_2$). Then each well was cleared of the solution, and washed three times with D-PBS. 200 μl/well of the B-E-NaPB was added, and incubated at 37° C. for 1 hour (blocking operation-1). Then each well was cleared of the B-E-NaPB to prepare a PUC2-$NH_2$-immobilized plate.
Into the PUC2-$NH_2$-immobilized plate, 100 μl/well of a 5×SSC solution containing 3.2 wt % of Polymer (P1) and 0.2 pmol/ml each of PUC, PUC', and PUC" was added, and incubated at 25° C. for 1 hour. Each well was cleared of the oligo DNA solution, and washed twice with a 30 mM sodium citrate solution containing 0.1% SDS and 300 mM NaCl at 25° C. 200 μl/well of the B-E-NaPB was added, and incubated at 37° C. for 30 minutes (blocking operation-2), and then each well was cleared of the B-E-NaPB. 100 μl/well of the Avidin-HRP solution was added, and incubated at 37° C. for 30 minutes (avidin-biotin reaction). Each well was then washed three times with D-PBS, 100 μl/well of the substrate solution included in the HRP kit was added, and the mixture was incubated at 25° C. for 10 minutes (POD-substrate reaction). Subsequently, 100 μl/well of the reaction terminator included in the HRP kit was added, and the absorbance at 450 nm was measured by means of SPECTRA MAX250 (microplate reader, manufactured by MOLECULAR DEVICES CORPORATION). Incidentally, the HRP kit used herein was Coloring Kit T for Peroxidase (manufactured by SUMITOMO BAKELITE CO., LTD.).
From the results of the measurements, the ratios of (absorbance of PUC)/(absorbance of PUC') and (absorbance of PUC)/(absorbance of PUC") were determined. The results are shown in Table 5.

Examples 3-2 to 3-9 and Comparative Examples 3-1 to 3-2

Measurements were made following the same procedures as in Example 3-1, except that Polymer (P1) was replaced with each polymer shown in Table 5. For Comparative Examples 3-1 and 3-2, only the ratio of (absorbance of PUC)/(absorbance of PUC") was determined. The results are shown in Table 5.

Comparative Example 3-3

Measurements were made following the same procedures as in Example 3-1, except that the 5×SSC solution containing 3.2 wt % of Polymer (P1) and 0.2 pmol/ml each of PUC, PUC', and PUC" was replaced with a 5×SSC solution containing 0.2 pmol/ml each of PUC, PUC', and PUC". The results are shown in Table 5.

Comparative Example 3-4

Measurements were made following the same procedures as in Example 3-1, except that the 5×SSC solution containing 3.2 wt % of Polymer (P1) and 0.2 pmol/ml each of PUC, PUC', and PUC" was replaced with a 5×SSC solution containing 1.0% casein (manufacture by SIGMA-ALDRICH CO.) and 0.1% N-LS (manufactured by WAKO PURE CHEMICALS INDUSTRIES, LTD.). The results are shown in Table 5.

Comparative Example 3-5

Measurements were made in the same way as in Example 3-1, except that the 5×SSC solution containing 3.2 wt % of Polymer (P1) and 0.2 pmol/ml each of PUC, PUC', and PUC" was replaced with 0.2 pmol/ml each of PUC, PUC', and PUC", and a 6×SSC solution containing 10 mg/ml Ficol 400 (manufactured by Amersham Pharmacia Biotech, trademark), 10 mg/ml polyvinylpyrrolidone, 10 mg/ml bovine serum albumin, and 0.5% SDS (Denhard's solution). The results are shown in Table 5.

TABLE 5

| | Kind of Polymer (Abbreviation) | (Absorbance of PUC)/(Absorbance of PUC') | (Absorbance of PUC)/(Absorbance of PUC") |
|---|---|---|---|
| Example 3-1 | (P1) | 5.1 | 2.3 |
| Example 3-2 | (P2) | 4.5 | 2.9 |
| Example 3-3 | (P3) | 3.1 | 2.5 |
| Example 3-4 | (P4) | 2.7 | 2.8 |
| Example 3-5 | (P6) | 4.2 | 3.0 |
| Example 3-6 | (P7) | 4.0 | 2.8 |
| Example 3-7 | (P8) | 3.6 | 2.6 |
| Example 3-8 | (P9) | 3.4 | 2.8 |
| Example 3-9 | (P10) | 3.6 | 2.8 |
| Comp. Ex. 3-1 | (P11) | — | 1.8 |
| Comp. Ex. 3-2 | (P12) | — | 2.0 |
| Comp. Ex. 3-3 | — | 2.0 | 1.0 |
| Comp. Ex. 3-4 | Other Inhibitor | 1.8 | 1.0 |
| Comp. Ex. 3-5 | Other Inhibitor | 1.6 | 1.0 |

From Table 5, it is understood that the ratios of the absorbance in full match (absorbance of PUC) to the absorbance in mismatch (absorbance of PUC' or PUC") are higher in Examples than in Comparative Examples. This means that the specific hybridization was not inhibited but the nonspecific hybridization was inhibited, thereby realizing more accurate hybridization.

What is claimed is:

1. A method of clinical analysis comprising the steps of:
(1) contacting a sample containing a specific nucleic substance with a test agent capable of hybridizing with said specific nucleic substance in the presence of polymer (H) having a nonspecific hybridization inhibitory action in an amount of 0.0001 to 20 wt % of a hybridization system, under particular conditions for hybridizing said specific nucleic substance with said test agent, and specifically hybridizing said nucleic substance with said test agent, while said polymer (H) inhibits nonspecific hybridization, wherein said polymer (H) has a weight average molecular weight of 1000 to 5000000 and has a group derived from a monomer having a phosphorylcholine-like group represented by the formula (1):

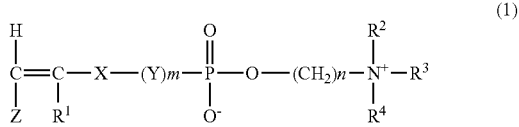

wherein X stands for a divalent organic residue, Y stands for an alkyleneoxy group having 1 to 6 carbon atoms, Z stands for a hydrogen atom or $R^5O(C=O)—$, provided that $R^5$ stands for an alkyl or hydroxyalkyl group having 1 to 10 carbon atoms; $R^1$ stands for a hydrogen atom or a methyl group, $R^2$, $R^3$, and $R^4$ are the same or different groups, and each stands for a hydrogen atom, or an alkyl or hydroxyalkyl group having 1 to 6 carbon atoms; m is 0 or 1, and n denotes an integer of 1 to 4, and (2) detecting a reactant generated by hybridization of said specific nucleic substance with said test agent in step (1).

2. The method according to claim 1, wherein said polymer (H) is a polymer obtained by polymerization of a monomer composition comprising 5 to 90 mol % of said monomer having a phosphorylcholine-like group represented by the formula (1), 5 to 90 mol % of at least one of a monomer having a carboxyl group and a monomer having a sulfone group, and 5 to 60 mol % of a hydrophobic monomer.

3. The method according to claim 2, wherein said monomer having a phosphorylcholine-like group represented by the formula (1) is 2-((meth)acryloyloxy)ethyl-2'-(trimethylammonio)ethyl phosphate, said monomer having a carboxyl group is (meth)acrylic acid, said monomer having a sulfone group is 2-methylpropane sulfonate, and said hydrophobic monomer is a monomer represented by the formula (2):

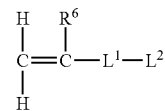

(2)

wherein $R^6$ stands for a hydrogen atom or a methyl group, $L^1$ stands for $-C_6H_4-$, $-C_6H_{10}-$, $-(C=O)O-$, $-O-$, $-(C=O)NH-$, $-O(C=O)-$, or $-O(C=O)O-$, and $L^2$ stands for a hydrogen atom, $-(CH_2)_g\text{-}L^3$, or $((CH_2)_p-O)_h\text{-}L^3$, wherein g and h each denotes an integer of 1 to 24, p denotes an integer of 3 to 5, and $L^3$ stands for a hydrogen atom, a methyl group, $-C_6H_5$, or $-OC_6H_5$.

* * * * *

SEQUENCE LISTING

<160> NUMBER OF SEQ ID NOS: 8

<210> SEQ ID NO 1
<211> LENGTH: 32
<212> TYPE: DNA
<213> ORGANISM: Artificial
<220> FEATURE:
<223> OTHER INFORMATION: synthetic oligonucleotide

<400> SEQUENCE: 1
actggccgtc gttttacaac gtcgtgactg gg                               32

<210> SEQ ID NO 2
<211> LENGTH: 20
<212> TYPE: DNA
<213> ORGANISM: Artificial
<220> FEATURE:
<223> OTHER INFORMATION: synthetic oligonucleotide

<400> SEQUENCE: 2
cccagtcacg acgttgtaaa                                             20

<210> SEQ ID NO 3
<211> LENGTH: 20
<212> TYPE: DNA
<213> ORGANISM: Artificial
<220> FEATURE:
<223> OTHER INFORMATION: synthetic oligonucleotide

<400> SEQUENCE: 3
cccagtcacc acgttgtaaa                                             20

```
<210> SEQ ID NO 4
<211> LENGTH: 20
<212> TYPE: DNA
<213> ORGANISM: Artificial
<220> FEATURE:
<223> OTHER INFORMATION: synthetic oligonucleotide

<400> SEQUENCE: 4
cccagtcacg tcgttgtaaa                                                   20

<210> SEQ ID NO 5
<211> LENGTH: 30
<212> TYPE: DNA
<213> ORGANISM: Artificial
<220> FEATURE:
<223> OTHER INFORMATION: synthetic oligonucleotide

<400> SEQUENCE: 5
cattagggat ccagccgtga attcgtcact                                        30

<210> SEQ ID NO 6
<211> LENGTH: 30
<212> TYPE: DNA
<213> ORGANISM: Artificial
<220> FEATURE:
<223> OTHER INFORMATION: synthetic oligonucleotide

<400> SEQUENCE: 6
agtgacgaat tcacggctgg atccctaatg                                        30

<210> SEQ ID NO 7
<211> LENGTH: 30
<212> TYPE: DNA
<213> ORGANISM: Artificial
<220> FEATURE:
<223> OTHER INFORMATION: synthetic oligonucleotide

<400> SEQUENCE: 7
gattttagct cttctttgga gaaagtggtg                                        30

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
tttacaacgt cgtgactggg                                                   20
```